United States Patent
Bruinsma et al.

(10) Patent No.: US 12,111,302 B2
(45) Date of Patent: Oct. 8, 2024

(54) DIAGNOSTIC ASSAY FOR RUMEN UNDEGRADED PROTEIN DETECTION

(71) Applicant: Novita Nutrition, LLC, Brookings, SD (US)

(72) Inventors: Keith E. Bruinsma, Brookings, SD (US); Donald L. Endres, Brookings, SD (US); Andrew James Manning, Sioux Falls, SD (US); Kurt M. Swenson, Beulah, ND (US)

(73) Assignee: Novita Nutrition, LLC, Brookings, SD (US)

( * ) Notice: Subject to any disclaimer, the term of this patent is extended or adjusted under 35 U.S.C. 154(b) by 534 days.

(21) Appl. No.: 17/285,460

(22) PCT Filed: Oct. 10, 2019

(86) PCT No.: PCT/US2019/055710
§ 371 (c)(1),
(2) Date: Apr. 14, 2021

(87) PCT Pub. No.: WO2020/081371
PCT Pub. Date: Apr. 23, 2020

(65) Prior Publication Data
US 2021/0341446 A1 Nov. 4, 2021

Related U.S. Application Data

(60) Provisional application No. 62/746,692, filed on Oct. 17, 2018.

(51) Int. Cl.
*G01N 33/02* (2006.01)
*G01N 27/447* (2006.01)
*G01N 33/68* (2006.01)

(52) U.S. Cl.
CPC ........... *G01N 33/02* (2013.01); *G01N 27/447* (2013.01); *G01N 27/44726* (2013.01); *G01N 33/6803* (2013.01); *Y10T 436/25375* (2015.01)

(58) Field of Classification Search
CPC .............. G01N 33/02; G01N 33/6803; G01N 33/6827; G01N 33/6839; G01N 27/447; G01N 27/44726; Y10T 436/25; Y10T 436/25375; Y10T 436/255
USPC ............. 436/20, 86, 87, 164, 174, 177, 178; 204/450, 456, 461, 463
See application file for complete search history.

(56) References Cited

U.S. PATENT DOCUMENTS 9,113,645 B2 * 8/2015 Bruinsma ............... C11C 1/025
2014/0274886 A1 * 9/2014 Weakley ............. A23K 20/147
426/2
2016/0262426 A1 * 9/2016 Bruinsma ............ A23K 20/142

FOREIGN PATENT DOCUMENTS

WO   WO 00/67017        11/2000
WO   WO 2014/159089 A1  10/2014
WO        2022/251779 A1 * 12/2022

OTHER PUBLICATIONS

Spencer et al. British Journal of Nutrition, vol. 60, 1988, pp. 241-247.*
PCT International Search Report for PCT/US2019/055710, mailed Feb. 5, 2020, 4 pages.
PCT Written Opinion of the International Searching Authority for PCT/US2019/055710, mailed Feb. 5, 2020, 6 pages.
Messman, M. A. et al., 'Use of electrophoresis to quantify ruminal degradability of protein from concentrate feeds', Animal Feed Science and Technology, 1994, vol. 49, pp. 25-35 abstract; and pp. 26-28.
Wang, Y. et al., 'Measurement of the intestinal digestibility of rumen undegraded protein using different methods and correlation analysis', Asian-Australasian Journal of Animal Sciences, Oct. 2015, vol. 28, No. 10, pp. 1454-1464 the whole document.
Chumpawadee, S. et al., 'Estimation of rumen undegradable protein with in situ nylon bag and in vitro enzymatic technique in tropical concentrate feedstuffs', Walailak Journal of Science and Technology, 2005, vol. 2, No. 1, pp. 23-33 the whole document.

* cited by examiner

*Primary Examiner* — Maureen Wallenhorst
(74) *Attorney, Agent, or Firm* — DeWitt LLP

(57) ABSTRACT

A diagnostic assay to determine a percentage rumen undegraded protein in a food product by comparing the percentage of modified protein content to the total crude protein content of the food product. The total crude protein content extracted from a food product sample prior to conducting gel electrophoresis to separate modified protein content from the total crude protein content. The gel band intensities of the separated protein contents analyzed to enumerate a ratio that is used to derive a correlated percentage numen undegraded protein for a given food product sample. The diagnostic assay capable of being provided onsite for quick, cost-efficient and accurate results.

21 Claims, 3 Drawing Sheets

GELCODE GLYCO STAIN
GLYCOPROTEIN STAIN
(STAINS SPECIFICALLY
GLYCOPROTEIN)

COOMASSIE BLUE
STANDARD PROTEIN STAIN
(STAINS ALL PROTEIN)

GELCODE GLYCO STAIN
GLYCOPROTEIN STAIN
(STAINS SPECIFICALLY
GLYCOPROTEIN)

COOMASSIE BLUE
STANDARD PROTEIN STAIN
(STAINS ALL PROTEIN)

DIAGNOSTIC ASSAY FOR RUMEN UNDEGRADED PROTEIN DETECTION

RELATED APPLICATION

This application is a national phase application under 35 U.S.C. § 371 of International Application No. PCT/US2019/055710, filed on Oct. 10, 2019 which claims the benefit of U.S. Provisional Patent Application No. 62/746,692, filed on Oct. 17, 2018, the contents of both of which are incorporated herein by reference in their entirety.

TECHNICAL FIELD

The present invention relates generally to the detection of rumen undegraded protein in a food product, more particularly in an animal feed or animal food product.

BACKGROUND

Digestion in animals occurs at a relatively fixed rate over time by a mixture of endogenous host enzymes, as well as the enzymes produced by the microbiota residing in an animal's rumen. As digestion occurs, proteins are broken down into peptides and amino acids, which are then either passed on in the intestinal tract of the animal or absorbed by the microbiota in the rumen. Protein that is highly modified by either enzymatic or chemical means is by its nature more challenging for the animal to digest.

Rumen undegraded protein ("RUP") is a subset of total protein that is protected from digestion in the rumen of an animal and is a key nutritional factor in delivering the necessary protein to animals. RUP protein are often referred to as bypass proteins, which are able to survive the rumen of a ruminant animal during the digestive process, such that more protein is bioavailable to the ruminant animal in the later stages of digestion in the small intestine, which results in greater protein absorption. Often the greater protein absorption occurs in the small intestine, which may increase milk production in dairy cattle, calf development and/or muscle generation.

RUP protein is comprised of a digestible portion and an indigestible portion. The digestible RUP (dRUP) contains protein that is available for absorption in the intestine, and units are often expressed on a dry matter (DM) basis. The nutritional value beyond having protected protein is that the digestion and breakdown of the protein for absorption in the diet is only nutritionally beneficial in the small intestine. Therefore, it is advantageous to decrease the digestibility in the rumen to increase the potential concentration of protein being delivered to the small intestine. RUP in a food product, including animal feed and animal protein supplements for ruminant animals, can be altered by many factors, including inbound ingredients, and temperatures and times during processing. Thus, food products including animal feed and animal protein supplements for ruminant animals need to be tested for the RUP content.

Current testing for nutritional determinations of larger populations of RUP generally involves either use of a ruminant animal, or a simulated ruminant system. Alternatively, some of these tests require use of a bag, pepsin, or the ability to evaluate amino acids.

One such test method to estimate intestinal digestibility of RUP is the mobile bag technique. However, animals must have ruminal duodenal and sometimes illeal cannulas, which can be invasive. As a result, this technique is limited to use in research settings having test animals.

Another method for measuring RUP, two step in vitro digestion, uses in vitro fermentation in rumen fluid to determine RUP as a first step. Then an acid digestion using pepsin is completed to determine the digestible portion. One inherent disadvantage with this technique is that a ruminant animal is needed.

Similar to the two step in vitro digestion method, a three step procedure is an alternative procedure for measuring RUP. The three step procedure uses an in situ bag technique (i.e., rumen incubation) as the first step. Then it follows with two steps in an in vitro system using hydrochloric acid and pepsin pre-digestion followed by pancreatin digestion. Digestion is terminated with trichloroacetic acid. Protein content is determined on the soluble fraction. However, a main drawback is that one cannot determine digestibility of amino acids with this technique.

An alternative to the traditional three step procedure is a modified three step procedure. A modified three step procedure performs post-rumen digestion steps from the three step procedure in an in vitro system called the Daisy incubator. The residue from in situ bag is placed in buffer-enzyme solutions to estimate intestinal digestibility without the need for trichloroacetic acid. Final residue is collected in a bag, which allows for further analysis of amino acids. This method also requires the use of a ruminant animal.

There are, however, several disadvantages associated with the foregoing techniques for measuring RUP. One inherent disadvantage with techniques using a bag is that soluble portions of the RUP fraction may be lost prior to the intestinal digestibility step (i.e., they escape the bag). The in situ bag also presents an additional disadvantage in that the in situ bag acts as a barrier to microbial movement, which results in longer fermentation lag times. Additionally, absence of protozoa from the in situ bag will underestimate degradation of the residue. Aside from disadvantages associated with in situ bags, these techniques also are costly and invasive, which makes it difficult to apply to routine analysis of feed samples. The techniques also take considerable time precluding quick turnaround times.

An additional RUP measuring method is precision-fed cecectomized rooster bioassay. This method provides an estimation of digestible RUP ("dRUP")—amino acids digestibility. Briefly, roosters are crop intubated with duodenal digesta collected from a ruminant animal, which stimulates intestinal digestion. Again, this method requires the use of a ruminant animal.

Two alternatives to the foregoing techniques that do not utilize a ruminant animal are the immobilized digestive enzyme assay ("IDEA") and the Ross method. IDEA is an in vitro assay which can estimate digestibility of protein and amino acids in feeds. This assay was initially developed for evaluation of human food, took around two and half days to complete, and incorporated a system of proteases immobilized on glass beads. IDEA kits have been developed for different protein supplements and provide a qualitative ranking or protein sources. However, quantitative information from IDEA kits is not validated with in situ data and is therefore not reliable. The Ross method begins with an in vitro incubation in rumen fluid to determine RUP followed by digestion steps. In short, digesta is acidified with hydrochloric acid and pepsin to simulate gastric digestion, the acid is neutralized and then a physiological enzyme mix (trypsin, chymotrypsin, amylase and lipase) is added. The resulting residue is the undigested residue. The difference between the RUP (% DM) and protein in the undigested residue (% DM) is the digestible RUP or dRUP. This assay can be completed in commercial laboratory settings, and there is the ability to test the residue for amino acids.

These aforementioned tests generally use a biological clock for determining digestibility, and thus can take beyond 16 hours for the testing to occur. Additionally, this testing is usually conducted by a third party and can take about 3 days, and as such, the turnaround time for shipment of a sample, testing and receiving results can be as long as 6 weeks.

Therefore, there is a need for a diagnostic assay for determining the percentage RUP of the crude protein in a food product without the disadvantages, including costs and long turnaround times of known RUP testing methods.

SUMMARY

The present invention is directed towards a method for testing a food product for rumen undegradable protein ("RUP"). In some aspects, the method comprises extracting a total protein content from an assay sample of the food product, wherein the total protein content comprises rumen undegraded protein. In some aspects the method comprises separating rumen undegraded protein from the total protein content by gel electrophoresis. In some aspects the method comprises staining an electrophoresis gel after separating rumen undegraded protein content. In some aspects, the stained electrophoresis gel may require destaining. In other aspects, the method comprises analyzing portions of protein present in the gel to determine a rumen undegraded protein content from the total protein content. In some other aspects, a ratio of glycosylated protein to the total protein content in the sample assay will provide a correlated value to the RUP content in the food product. In some aspects, the ratio of glycosylated protein to the total protein content in the sample assay are compared to third-party testing results to derive a correlation for determining the RUP value.

Enzymatic digestibility kinetics of products such as a food product often depends upon the availability of the protein to be cleaved by enzymatic means. Typically, the chemical reaction that is driven by these enzymes requires free ends on the amino acids that are terminal in the cleavage. In some aspects, advanced protein modification is driven by the chemical process known as the Maillard reaction, whereby free amine and hydroxyl groups can have sugars and/or fiber attach to a protein.

The Maillard reaction results in protein glycation, or the addition of sugar moieties to the protein on amino acids with a free terminal nitrogen ("N") or oxygen ("O"). Glycation is a chemical reaction derivative of the enzymatic process known as glycosylation and is characterized by the addition of free or chained sugars to the protein. The reaction is driven by available fiber, sugar, water, protein, and heat, and can result in a highly modified protein that in turn is less able to be digested by biological enzymatic processes. In some aspects, digestion is limited by modifications on amino acids that are required to have a free amine or hydroxyl end to help catalyze the reaction resulting in digested protein.

In some aspects, the likely source of modification of amino acids is sugar based, and this principle can be used to determine a correlation between degree of modification and percentage of RUP. Therefore, in some aspects, the ratio of glycosylated protein can be compared to the total protein present in a food product. In some aspects, the correlation of glycosylated protein to the total protein gives a strong correlation to the RUP value of protein present in a food product.

In some aspects, looking at RUP in the foregoing manner shortens the time for testing to less than 3 days, in some aspects less than 2 days, in some aspects less than about one and a half days, and in some aspects to about 1 day, and drastically reduces costs associated with RUP diagnostic assays. In some aspects, further analysis of the type and amount of modification can lead to a further understanding of digestible RUP.

In some aspects, a food product can be ground to a fine powder using liquid nitrogen. In other embodiments, a food product can be ground using any suitable method that will produce a fine powder. Using an extraction buffer, a sample of the ground food product may be boiled and then centrifuged. In some aspects, use of an extraction buffer maximizes the amount of protein extracted from the sample. In some aspects, after centrifugation, the aqueous phase of the extraction is aspirated.

In some aspects, following extraction of the total protein content, the sample is prepared for electrophoresis by the addition of a sample buffer and subsequent boiling. In some aspects the method of electrophoresis is SDS-PAGE electrophoresis. The sample is then loaded onto a gel and run in a buffer solution. In some aspects, the gel can be anywhere from about 4% to about 12% acrylamide. In some aspects the gels are run in duplicate, with the same amount of sample applied to each gel. In some aspects, duplicated running of gels allows examination of a desired protein in the same manner as the total protein content. In some aspects, the desired protein is a modified protein, in some aspects the modified protein is glycosylated protein.

In one aspect, a gel is dyed with a glycoprotein stain to test for a modified protein content, which in some aspects is glycosylated protein. In another aspect, a gel is stained with a general protein stain to test for total protein content. In some aspects, the stain used for a general protein is a Coomassie protein stain.

In some aspects, once the gels and respective protein band portions on the gels are stained, the gels undergo destaining to remove unwanted stain from the gel while retaining the stained protein band portions.

In some aspects, once the gels are stained and de-stained, the samples are imaged, and the images are analyzed for band intensity across the entirety of the gel lane. In some aspects, analyzing the band intensity accounts for the same protein population between the two gels and allows normalization of the intensity of the modified protein to the total protein. In some aspects the ratios derived between the protein band portions concerning the modified protein content and the total protein content are used to determine the RUP value in the sample assay.

In some aspects, the ratio derived from the two gels are then plotted against third party testing results to derive a correlation. In some aspects, with a good correlation, a consistent RUP value for any given sample can be determined.

In some aspects, by examining RUP by obtaining a sample of a food product, buffering, electrophoresis, and using the ratio against a correlation chart of the extracted protein, the methodology of RUP analysis can be simplified such that the analysis can be done in-house in an expeditious manner. Additionally, in some aspects, this method of analysis allows for improved turnaround time and reduction of costs.

Other features and advantages of the invention will become more apparent from the following description thereof, given only for illustrative and in no way restrictive purposes, with reference to several embodiments illustrated in the accompanying drawings, in which:

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
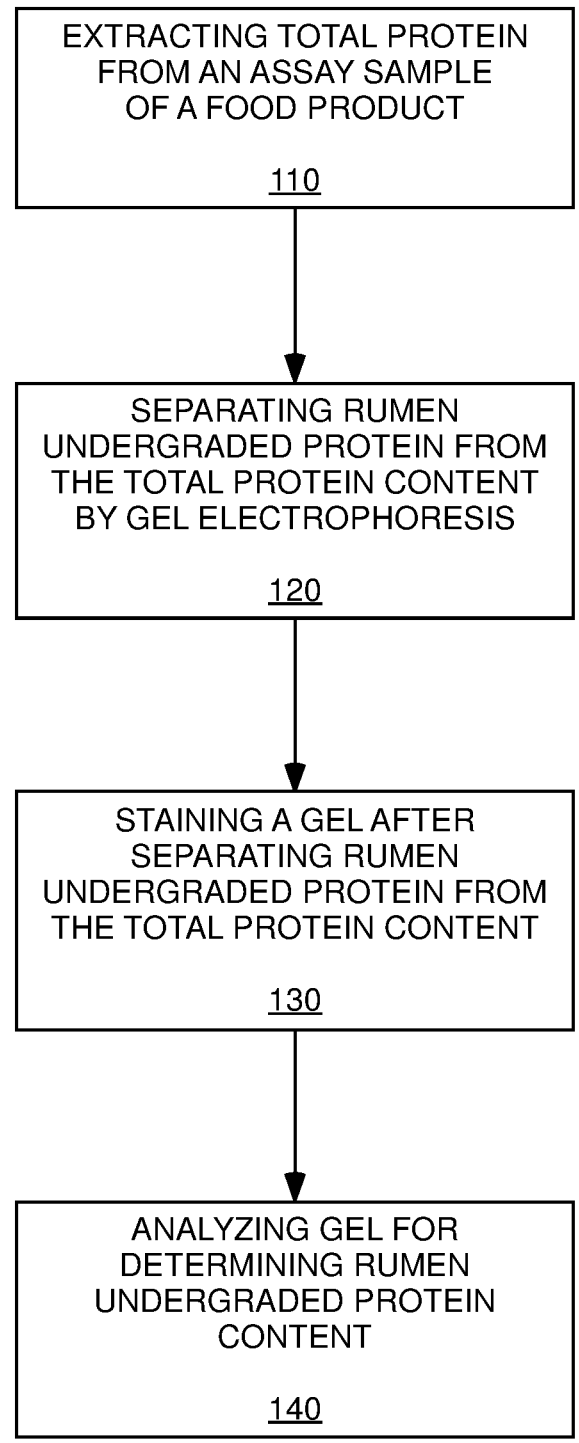
FIG. 1 is a flow diagram illustrating the diagnostic assay according to certain aspects of the present invention.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

It will be readily understood that the methods and materials as they are generally described and illustrated in the figures herein could be arranged and designed in a wide variety of different configurations. Thus, the following more detailed description of various embodiments of the methods and materials provided herein is not intended to limit the scope of the claims, but merely provides representative examples of various embodiments of the subject matter recited in the appended claims. For example, though a food product is referenced as a source feed herein, it is to be understood that other feeds can be utilized instead of or in addition to a food product. Also, though SDS-PAGE electrophoresis is referenced as a method of electrophoresis, it is to be understood that other methods of electrophoresis can be used. Further, though a glycoprotein stain and Coomassie protein stain are mentioned, it should be understood that any other protein stain suitable for staining modified proteins and total protein could be used. Thus, the following description, while specific to a food product and use of SDS-PAGE electrophoresis and glycoprotein and Coomassie protein stains, it should also be understood that other feeds, methods of electrophoresis and protein stains can be used without departing from the scope and spirit of the presently described invention.

Referring now to the Figures, FIG. 1 depicts a flow chart of a method for testing a food product for rumen undegraded protein ("RUP"). In one aspect, a method for testing a food product for RUP may comprise extracting a total protein from an assay sample of a food product 110, separating rumen undegraded protein from the total protein content by gel electrophoresis 120, staining a gel after separating rumen undegraded protein from the total protein content 130, and analyzing the gel for determining rumen undegraded protein content 140. The method may further optionally comprise washing the assay sample after the total protein content is extracted from the assay sample. The method may further comprise de-staining one or more gels. The gels may also be imaged in order to analyze band intensities of the gels across the gel lane. A ratio of the band intensities may be plotted against results using another testing methodology to derive a correlation to determine a consistent RUP value for a given assay sample.

In a food product, protein that is highly modified by either enzymatic or chemical means is by its nature more challenging for an animal to digest. As certain food products undergo processing, there may be an increase in RUP derived by protein modification, such as the Maillard reaction. The Maillard reaction results in protein glycation, or the addition of sugar moieties to the protein on amino acids with a free terminal nitrogen or oxygen. Glycation is a chemical derivative of the enzymatic process known as glycosylation and is characterized by the addition of free or chained sugars to the protein. As this is a common protein modification, without wishing to be bound by theory, it is believed that a comparison of the ratio of glycosylated protein content to the total protein content of a food product provides a strong correlation to the RUP value of the food product.

Food Product Preparation

A food product for the diagnostic assay of the present invention can be any food product containing one or more proteins. In some preferred aspects of the present invention, the food product is a natural source product originally derived from one or more plant, animal or fermentation sources. In some preferred aspects of the present invention, the food product is a natural source product, preferably a natural source product originally derived from an ethanol fermentation source. In some aspects, the fermentation source may be corn, surgarcane, potato, cassava, hemp, wheat, grain sorghum, barely, fruit or other sugar or starch crops. In some aspects, the food product is an animal feed product or an animal feed supplement derived from one or more plant, animal or fermentation sources. In certain aspects, the food product may be distillers meal, corn distillers meal, distillers dried grains, distillers dried grain with solubles, or mixtures and combinations thereof. In some aspects, the distillers meal, corn distillers meal, distillers dried grains or distillers dried grains with solubles can be provided as disclosed in U.S. Patent Application Publication No. 2016/0262426 A, the contents of which are incorporated by reference herein. An assay sample for the present diagnostic assay may be provided from the food product in its existing form, or alternatively, the food product may be processed to a desired particle size before the step of extracting a total protein from an assay sample of a food product 110.

In some aspects, the food product is processed to a desired particle size using conventional processing techniques, including milling, fluid energy milling, grinding, roller milling, hammer milling, and the like. In some aspects, the food products are processed to have a particle size from about 50 microns to about 200 microns, preferably about 75 microns to about 175 microns, preferably about 90 microns to about 100 microns, more preferably about 50 microns to about 90 microns.

In one aspect of the present invention, the food product may be provided at a desired particle size by grinding the food product, such as using a FOSS Cemotec™ grinder followed by using a mortar and pestle and liquid nitrogen to provide a fine uniform powder having an average particle size of about 50 microns to about 200 microns, preferably about 75 microns to about 175 microns, preferably about 90 microns to about 100 microns, more preferably about 50 microns to about 90 microns. In some aspects, the food product is cooled prior to or during grinding to a temperature less than 0° C., preferably using liquid nitrogen, liquid carbon dioxide, or another suitable inert cooling medium.

Extraction of Protein

According to certain aspects of the present invention, a total protein is extracted from the food product 110. The protein may be extracted from the food product by a chemical protein extraction process. The chemical extraction process may utilize an extraction buffer.

In certain aspects, the extraction buffer is chosen to extract the greatest quantity of all protein from the assay sample. In some aspects, the extraction buffer comprises one or more of ethylenediamine tetra acetic acid, Tris-HCl, sodium dodecyl sulfate, and β-mercaptoethanol. In certain preferred aspects of the present invention, the extraction buffer comprises ethylenediamine tetra acetic acid, Tris-HCl, sodium dodecyl sulfate, and β-mercaptoethanol. In some aspects, the extraction buffer may also comprise glycerol.

The chemical extraction process may comprise mixing an aliquot of the extraction buffer with a desired amount of sample assay in a desired vessel, such as a sample tube. For example, a test tube may comprise an assay sample of about 0.15 to about 0.50 grams, more preferably about 0.20 to about 0.40 grams, more preferably about 0.25 to about 0.30 grams, to which the extraction buffer aliquot is added. In some aspects, at least 200 µL, at least 300 µL, at least 400 µL, at least 500 µL, at least 600 µL, at least 700 µL, at least 800 µL, at least 900 µL, of the extraction buffer is mixed with the sample assay. In some aspects, up to 5 ml, up to 4 ml, up to 3 ml, up to 2 ml, up to 1.5 ml, up to 1 ml, of the extraction buffer is mixed with the sample assay. In some aspects, about 200 µL to about 5 ml, about 250 µL to about 4 ml, about 300 µL to about 3 ml, about 500 µL to about 1 ml, about 700 µL to about 800 µL, of the extraction buffer is mixed with the sample assay.

In certain aspects, a means of mixing is used to thoroughly mix the assay sample and extraction buffer to allow maximum extraction of all protein from the assay sample into the liquid phase. In some aspects, the extraction buffer and sample assay are mixed using a stir stick, a vortex mixer, a mixing plate with a magnetic stirring rod, a static mixer, or a shaker.

Prior to the mixing process, during the mixing process and/or after the mixing process, the sample may be heated to optimize extraction of the protein into the liquid phase. In some aspects, the sample may be heated to a temperature in the range of about 50° C. to about 120° C., preferably about 60° C. to about 110° C., more preferably about 80° C. to about 100° C., more preferably about 90° C. to about 95° C. In some aspects, the sample is heated for a period of time of about 2 minutes to about 2 hours, preferably about 5 minutes to about 60 minutes, preferably about 7 minutes to about 15 minutes, more preferably about 9 minutes to about 11 minutes. In some aspects, the sample may be heated to a temperature up to about 100° C. for a period of time of about 15 minutes or less. In some aspects, the sample may be heated to a temperature between about 50° C. and about 100° C. for a period of time of at least 2 minutes up to about 15 minutes.

After appropriate mixing and/or heating, the sample may be cooled and centrifuged to separate the liquid phase from the solid sample phase. In some aspects, the sample is centrifuged at a temperature between about 0° C. to about 21° C., preferably about 1° C. to about 15° C., preferably about 2° C. to about 10° C., preferably about 3° C. to about 5° C. In some aspects, the sample is centrifuged for a period of time of about 1 minute to about 30 minutes, preferably about 2 minutes to about 20 minutes, more preferably about 5 minutes to about 15 minutes.

The liquid phase may be aspirated from the top of the sample and collected. The steps of mixing the sample assay with an extraction buffer, heating, centrifuging and aspirating the liquid phase may be repeated at least once, preferably at least twice, more preferably at least three times, and more preferably at least four times, to maximize extracting as much protein as possible from the sample assay. Each time these steps are repeated, the collected liquid phase may be combined with the other collected liquid phase.

Sample Washing

According to certain aspects of the present invention, the remaining assay sample may optionally be further washed to remove any additional residue protein content after the protein extraction using the extraction buffer. In certain aspects, the remaining assay sample may be washed with a washing buffer. In some aspects, the extraction buffer comprises a reagent at a pH between about 5.5 and 7.5, preferably between about 6.0 and 7.0, more preferably between 6.5 and 7.0. In some aspects, the extraction buffer comprises Tris-HCl. In some aspects, the extraction buffer for the sample washing is the same as the extraction buffer for the extraction of protein.

The sample washing process may comprises mixing an aliquot of the washing buffer with the remaining assay sample in the same or different vessel, such as a sample tube. For example, a test tube may comprise the remaining assay sample to which the washing buffer aliquot is added. In some aspects, at least 200 µL, at least 300 µL, at least 400 µL, at least 500 µL, at least 600 µL, at least 700 µL, at least 800 µL, at least 900 µL, of the washing buffer is mixed with the remaining sample assay. In some aspects, up to 5 ml, up to 4 ml, up to 3 ml, up to 2 ml, up to 1.5 ml, up to 1 ml, of the washing buffer is mixed with the remaining sample assay. In some aspects, about 200 µL to about 5 ml, about 250 µL to about 4 ml, about 300 µL to about 3 ml, about 500 µL to about 1 ml, about 700 µL to about 800 µL, of the washing buffer is mixed with the remaining sample assay.

In certain aspects, a means of mixing is used to thoroughly mix the remaining assay sample and washing buffer to allow maximize extraction of any additional protein from the remaining assay sample into the liquid phase. In some aspects, the washing buffer and remaining sample assay are mixed using a stir stick, vortex mixer, a mixing plate with a magnetic stirring rod, a static mixer, or a shaker.

Prior to, during, and/or after the mixing process, the sample may be optionally heated to optimize extraction of any additional protein to the liquid phase. In some aspects, the sample may be heated to a temperature in the range of about 50° C. to about 120° C., preferably about 60° C. to about 110° C., more preferably about 80° C. to about 100° C., more preferably about 90° C. to about 95° C. In some aspects, the sample is heated for a period of time of about 2 minutes to about 2 hours, preferably about 5 minutes to about 60 minutes, preferably about 7 minutes to about 15 minutes, more preferably about 9 minutes to about 11 minutes. In some aspects, the sample may be heated to a temperature up to about 100° C. for a period of time of about 15 minutes or less. In some aspects, the sample may be heated to a temperature between about 50° C. and about 100° C. for a period of time of at least 2 minutes up to about 15 minutes. In some aspects, the sample is heated to the same temperature for the same period of time as the extraction of protein sample.

The sample may be centrifuged to separate the liquid phase from the remaining solid sample phase. In some aspects, the sample is centrifuged at a temperature between about 0° C. to about 21° C., preferably about 1° C. to about 15° C., preferably about 2° C. to about 10° C., preferably about 3° C. to about 5° C. In some aspects, the sample is centrifuged for a period of time of about 1 minute to about 30 minutes, preferably about 2 minutes to about 20 minutes, more preferably about 5 minutes to about 15 minutes.

The liquid phase may be aspirated from the top of the sample and collected. The steps of mixing the sample assay with a washing buffer, optional heating, centrifuging and aspirating the liquid phase may be repeated at least once, preferably at least twice, more preferably at least three times, and more preferably at least four times, to maximize extracting all remaining protein from the remaining sample assay. Each time these steps are repeated, the collected liquid phase may be combined with the other collected liquid phase. The collected liquid phase preferably remains separate from the collected liquid phase of the extraction process. In an alternative embodiment, the collected liquid phases may be combined with the collected liquid phase of the extraction process.

Gel Electrophoresis

The collected samples from the extraction process and/or washing process may undergo gel electrophoresis to separate the rumen undegraded protein from the total protein content 120. In some aspects, the collected samples undergo gel electrophoresis on duplicate gels. In some aspects, the gel electrophoresis comprises SDS-gel electrophoresis. In some aspects, the gel electrophoresis is a polyacrylamide gel electrophoresis. In some aspects, the gel electrophoresis is a sodium dodecyl sulfate-polyacrylamide gel electrophoresis. In some aspects, a polyacrylamide percentage of the sodium dodecyl sulfate-polyacrylamide gel electrophoresis is between about 4% and 20% polyacrylamide. In some aspects, the gel electrophoresis is a tris-glycine gel electrophoresis, such as Novex™ Tris-Glycine Gels available from ThermoFisher Scientific™.

In some aspects, the collected samples from the extraction process and/or washing process may be mixed with a sample buffer for gel electrophoresis. In some aspects, the sample buffer comprises sodium dodecyl sulphate, β-mercapto ethanol, bromophenol blue, glycerol, and tris-glycine at pH of about 6.8. In certain aspects, about 15 µL to about 25 µL, preferably about 20 µL, of the collected samples mixed with the sample buffer and are loaded onto at least one gel. In some preferred aspects the collected samples are mixed with the sample buffer are loaded on duplicate gels. In some aspects, the gels are preferably run in duplicate to accommodate separate staining for the modified protein and all protein under identical running conditions. In some aspects, glycostain positive and negative controls are also loaded onto the duplicate gels.

After loading the samples and controls, the gel electrophoresis is conducted until the dye front is at the bottom of the gel, but has not run off the gel. In some aspects, voltage is applied to the gel in a range of about 1 to 1000 volts, preferably 105 volts to about 140 volts for a desired period of time. In some aspects, the voltage applied to the gel is varied in a range of about 105 volts to about 140 voltes, preferably between about 108 volts to about 112 volts, more preferably between about 109 volts to about 111 volts, most preferably about 110 volts, for a period of time between greater than 1 minute up to about 60 minutes, preferably about 15 to about 25 minutes, preferably about 20 minutes, followed by a voltage between about 125 volts to about 135 volts, more preferably between about 128 volts and about 132 volts, most preferably about 130 volts for the remainder of the gel. In some other aspects, a voltage of 110 volts is applied for about 20 minutes at which time the voltage is increased to 130 volts for the remainder of the time. In some aspects, the duplicate gels undergo the same voltage and time periods during the gel electrophoresis.

Gel Staining and De-Staining

The gels are stained upon completion of the gel electrophoresis to separate the rumen undegraded protein from the total protein content 130. In some aspects, one gel is stained with a stain that stains all protein content, while the other gel is stained with a stain that only stains modified protein content. In some aspects, the stain only stains glycosylated protein.

In some aspects, the stain used to stain all protein content comprises glacial acetic acid, methanol, water and a dye. In some aspects, the dye is R250. In some aspects, the stain used to stain all protein content is Coomassie Blue Stain.

In some aspects, the stain used to stain only the modified protein content is a glycoprotein stain. In some aspects, the glycoprotein stain is capable of staining glycosylated proteins in a polyacrylamide gel. A representative glycoprotein stain is Pierce Glycoprotein Staining Kit No. 24562 commercially available from ThermoFisher Scientific™.

In some aspects, one of the duplicate gels is placed in a prepared Coomassie stain and set for about 3 to about 24 hours. In some aspects, one of the duplicate gels is placed in a prepared Pierce Glycoprotein staining kit as previously described for about 2.5 to about 28 hours.

In the event one or more of the stains also stains the gel instead of the desired protein band, the one or more gels may be de-stained. In some aspects, stains may be used that stain the proteins without staining the gel, such that de-staining is unnecessary. In some aspects where the stain also stains the gel, the de-stain can be applied over a desired period of time to de-stain the gels.

In one aspect, the Coomassie stain and gel is de-stained using de-stain over a time period of about 24 hours. In some aspects, the de-stain is replaced at least once as the Coomassie gel is de-stained. In some aspects, the de-stain is replaced at least once as the Pierce Glycoprotein gel is de-stained.

Intensity Analysis

Upon completion of the gel electrophoresis with appropriate staining and any necessary de-staining, the gels may be analyzed for determining rumen undegraded protein content 140. In some aspects, photographic images of the gels are taken. In some aspects, a photographic image is taken of the gel with all protein content stained. In some aspects, a photographic image is taken of the gel with only the modified protein content stained. In another aspect, photographic images of the duplicate gels with different stains are taken in the same conditions and lighting and with the same equipment.

The intensity of the protein bands on the gels from the photographic images can then be analyzed using computer software. In some aspects an intensity analysis of the gel with all protein content stained and gel with only the modified protein content stained is conducted using J-imaging software. In other aspects, any other suitable imaging software may be used to conduct the intensity analysis.

In one aspect, the photographic images of the gel with all protein content stained and the gel with only the modified protein content stained can be translated to black-and-white or grayscale images. In one aspect, the entirety of each gel lane corresponding to the respective sample is boxed out and the total intensity of each translated image is measured to normalize the intensity of the modified protein content to the all protein content. In some other aspects, a ratio of the glycosylated protein band to the total protein band between the duplicate gels will provide a correlated value to the RUP content in the food product.

Figure 4:
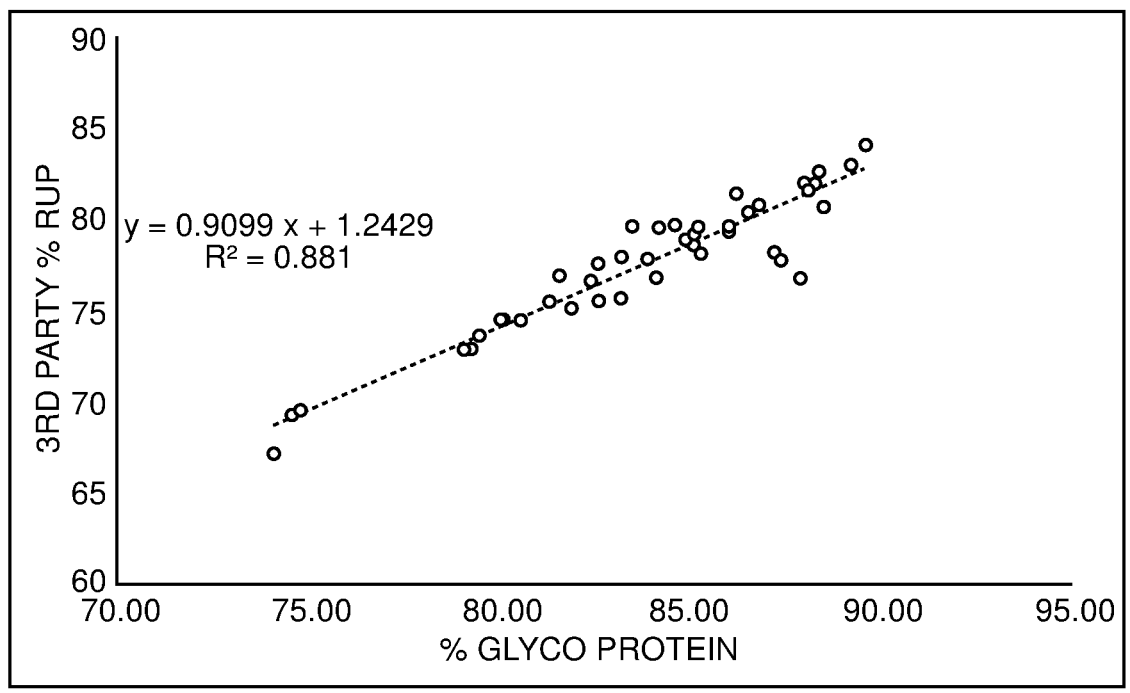
FIG. 4 is a correlation chart for determining the RUP content in a food product sample using third party RUP values as compared to a derived Coomassie/Glycoprotein ratio, according to certain aspects of the present invention.

In some aspects, the band intensity ratios between the modified protein content and the all protein content can be plotted against a third party RUP testing method to derive a correlation, which can be used to determine a consistent RUP value of any given sample. In FIG. 4, a correlation chart for determining the RUP content in a food product sample using third party RUP values as compared to a derived Coomassie/Glycoprotein band intensity ratio is shown.

The invention is further illustrated in the following non-limiting example.

EXAMPLE

A food product was analyzed according to methods of the present invention to determine the rumen undegraded protein content. A NovaMeal™ feed pellet (derived from dried distillers grains with solubles) was ground using a FOSS Cemotec Grinder on a number 4 setting. Using a mortar and pestle, 20 mL of liquid nitrogen and 20 g of the sample were further ground to a fine, uniform powder. The sample was then weighed and 0.25 g of the ground sample was placed in a 1.5 mL Eppendorf tube. The weight was then recorded again.

An extraction buffer was prepared from 0.05M EDTA with a pH of 8.0, 0.03M Tris-HCL with a pH of 6.8, 4% (m:v) Sodium Dodecyl Sulfate, 1% (v:v) β-mercaptoethanol, and 5% glycerol. 750 μL of the prepared extraction buffer was added to the sample tube and vortexed for 20-30 seconds. The cap on the Eppendorf tube was locked and the tube was placed in a 90° C. heat block for 10 minutes. After the sample was heated, the sample was then centrifuged at 4° C. for 10 minutes at a max speed of 13,000 g. Following centrifugation, any liquid remaining on the top of the sample was aspirated off and subsequently put into a 15 mL conical tube. The steps of adding prepared extraction buffer and vortexing, heating, centrifuging and aspirating were repeated a total of 4 times, with each collection of aspirated liquid being placed into the same 15 mL conical tube.

After the steps of protein extraction from the sample were completed, a washing buffer was prepared. The washing buffer was prepared from 0.12M Tris-HCl with a pH of 6.8. 750 μL of washing buffer was then added to the sample tube. The tube volume was mixed by pipetting up and down and stirring with a pipette tip. The sample was then centrifuged for 2 minutes at 4° C. at a max speed of 13,000 g. Following centrifugation, any liquid remaining on the top of the sample was aspirated off and subsequently put into a 15 mL conical tube. The steps of adding the washing buffer, mixing, centrifuging and aspirating were repeated a total of 4 times, with each collection of aspirated liquid being placed into the same 15 mL conical tube.

Following the steps of washing, a 4X-sample buffer was prepared. The buffer was prepared from 277.8 mM Tris-HCL with a pH of 6.8, 44.4% (v:v) Glycerol, 4.4% (w:v) Sodium Dodecyl Sulfate, 0.02% Bromophenol Blue, and 10% (v:v) β-mercaptoethanol. The 4X-sample buffer was then added to the conical tube containing the liquid aspirated from the sample tube following the extraction step such that the total volume of liquid in the tube equaled 100 μL. The 4X-sample buffer was then added to the conical tube containing the liquid aspirated from the sample tube following the washing step such that the total volume of liquid in the tube equaled 100 μL.

Following mixing of each the extraction sample and wash sample with the 4X-buffer, Glycostain positive and negative controls and 12% tris SDS-PAGE Gel were prepared. 20 μL of each sample was loaded onto two SDS-Page gels. Each gel was in the same positioning, such that each gel was identical loaded with the exact same sample run. Each gel was run at 110 volts for 20 minutes, then increased to 130 volts for the remainder of the gel. The gel was run until the dye front was at the bottom of the gel, but stopped before the sample ran off the gel.

A Coomassie blue stain was then prepared from 100 mL Glacial Acetic Acid, 450 mL Methanol, 450 de-ionized water, and 0.25 g R250 Dye. One of the duplicate gels was placed in the Coomassie stain and the gel was stained overnight. The other gel was stained using Pierce Glycoprotein staining kit Thermo #24562.

A De-stain was prepared from 100 mL Glacial Acetic Acid, 350 mL Methanol, and 550 mL de-ionized water, and the Coomassie gel was de-stained over the course of one day, with the de-stain replaced multiple times throughout the day.

Figure 2A:
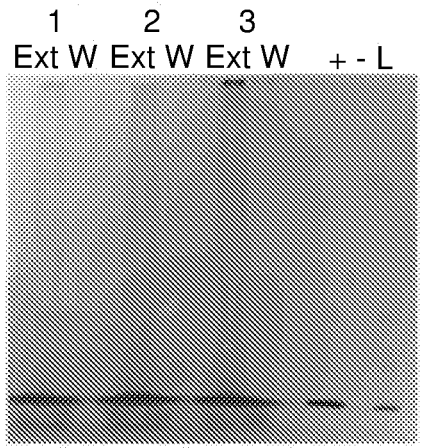
FIGS. 2A and 2B are images of duplicate stained electrophoresis gels after conducting gel electrophoresis on an extracted sample loaded onto the gels, one gel stained with a standard Coomassie protein stain and the other gel stained with a glycoprotein stain, according to certain aspects of the present invention.
Figure 2B:
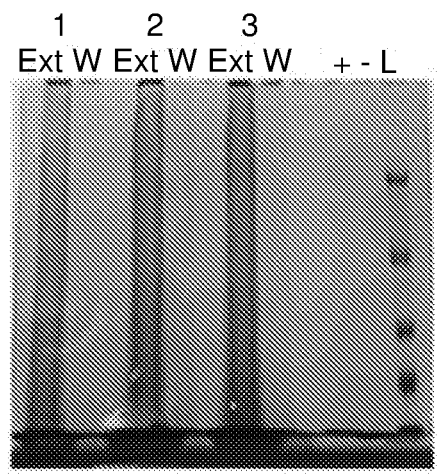
Figure 3A:
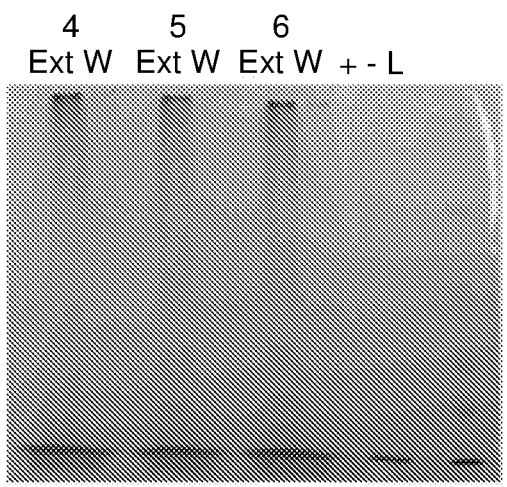
FIGS. 3A and 3B are images of duplicate stained electrophoresis gels after conducting gel electrophoresis on an extracted sample loaded onto the gels, one gel stained with a standard protein stain and the other gel stained with a glycoprotein stain, according to certain aspects of the present invention.
Figure 3B:
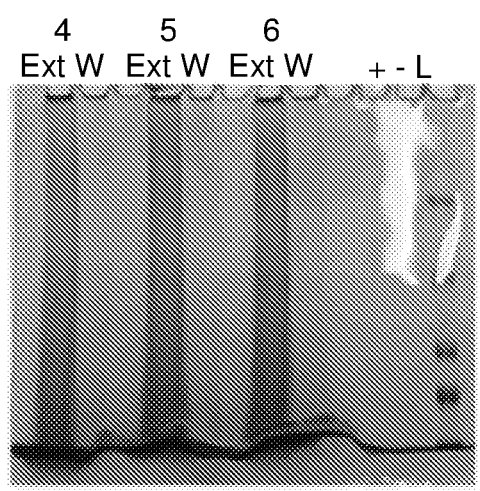

Photographic images of the gels were taken using the same lighting and conditions with the same camera, which are shown in FIGS. 2A and 2B. On the images of the gels, "Ext W" means Extraction Wash, "+" means positive glycoprotein control, and "−" means negative gylcoprotein control.

The gels were then analyzed using Image J imaging software and translated into grayscale and black and white. Each gel stain lane was boxed out and the total intensity was measured. The measurement of glycol-stained intensity over the total protein intensity was taken and plotted versus a third party lap RUP (% CP) value, as shown in FIG. 4. As provided in Table 1, the RUP value from samples 1, 2, and 3 was closely correlated with the calculated percent glycoprotein from the duplicate electrophoresis gels.

TABLE 1

Comparison of CVAS RUP and Calculated % Glycoprotein in a NovaMeal™ sample.

| Sample | CVAS RUP (% CP)Value | Calculated % Glycoprotein |
|---|---|---|
| 1 | 79.60 | 86.01 |
| 2 | 80.80 | 87.97 |
| 3 | 73.50 | 77.66 |

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A method for testing a food product for rumen undegraded protein, the method comprising:
   extracting a total protein content from an assay sample of the food product to provide an extraction sample, wherein the total protein content of the extraction sample comprises a rumen undegraded protein content;
   conducting gel electrophoresis on the extraction sample applied to a first gel and a second gel to separate the rumen undegraded protein content from the total protein content, thereby providing a residual total protein content;
   staining the first gel after separating the rumen undegraded protein content from the total protein content, wherein staining the first gel comprises applying a stain capable of staining glycosylated proteins in a polyacrylamide gel such that the stained glycosylated proteins correspond to the separated rumen undegraded protein content;
   staining the second gel after separating the rumen undegraded protein content from the total protein content, wherein staining the second gel comprises applying a stain capable of staining the total protein content in the extraction sample including both the separated rumen undegraded protein content and the residual total protein content in a polyacrylamide gel;
   and conducting an intensity analysis of the stained separated rumen undegraded protein content in the first gel and the stained total protein content in the second gel to determine a percentage of rumen undegraded protein in the total protein content of the food product.

2. The method of claim 1, wherein the food product is selected from an animal feed product and an animal feed supplement.

3. The method of claim 1, wherein the food product is a byproduct derived from an ethanol fermentation process.

4. The method of claim 3, wherein the food product is distillers meal or corn distillers meal.

5. The method of claim 1, further comprising prior to the extracting, preparing the assay sample comprising grinding at least a portion of the food product to a particle size ranging from about 50 microns to about 200 microns to prepare the assay sample.

6. The method of claim 5, wherein the portion of the food product is cooled during grinding to a temperature less than 0° C. using liquid nitrogen or liquid carbon dioxide.

7. The method of claim 1, wherein extracting a total protein content comprises mixing an extraction buffer with the assay sample.

8. The method of claim 7, wherein the extraction buffer comprises one or more of ethylenediamine tetra acetic acid, Tris-HCl, sodium dodecyl sulfate, and ß-mercaptoethanol.

9. The method of claim 7, wherein extracting a total protein content further comprises heating the assay sample mixed with the extraction buffer to a temperature range of about 50° C. to about 120° C.

10. The method of claim 9, wherein after the heating, extracting a total protein content further comprises cooling the assay sample mixed with the extraction buffer to a temperature between about 0° C. and about 21° C. and then centrifuging the assay sample mixed with the extraction buffer.

11. The method of claim 10, wherein after the assay sample mixed with the extraction buffer is centrifuged, extracting a total protein content further comprises aspirating a first liquid phase from the assay sample and collecting the first liquid phase to provide the extraction sample.

12. The method of claim 11, wherein extracting a total protein content is repeated at least once before conducting gel electrophoresis on the extraction sample.

13. The method of claim 11, further comprising washing a residual assay sample defined by the assay sample after collection of the first liquid phase to provide the extraction sample, wherein washing the residual assay sample comprises mixing the residual assay sample with a washing buffer to provide a washed assay sample.

14. The method of claim 13, wherein washing the residual assay sample further comprises centrifuging the washed assay sample, aspirating a second liquid phase from the centrifuged washed assay sample and then collecting the second liquid phase and combining it with the first liquid phase to provide the extraction sample.

15. The method of claim 14, wherein washing the residual assay sample is repeated at least once.

16. The method of claim 14, wherein conducting gel electrophoresis is conducted on the combined first and second liquid phases to separate a rumen undegraded protein content from the total protein content.

17. The method of claim 14, wherein the gel electrophoresis is a sodium dodecyl sulfate-polyacrylamide gel electrophoresis having a polyacrylamide percentage of the sodium dodecyl sulfate-polyacrylamide gel electrophoresis between about 4% and 12% polyacrylamide.

18. The method of claim 1, further comprising mixing the extraction sample with a sample buffer prior to conducting gel electrophoresis wherein the sample buffer comprises one or more of Tris-HCl, glycerol, sodium dodecyl sulfate, bromophenol blue, and ß-mercaptoethanol.

19. The method of claim 1, wherein conducting gel electrophoresis on the extraction sample is conducted at a voltage range of about 90 volts to 130 volts until the extraction sample migrates from a starting point to an end point on the first and second gels.

20. The method of claim 1, further compromising de-staining the first and second gels using a de-stain.

21. The method of claim 1, wherein the intensity analysis comprises comparing a band intensity of the stained separated rumen undegraded protein content in the first gel to a band intensity of the total protein content in the second gel.

\* \* \* \* \*